US006436421B1

(12) United States Patent
Schindler et al.

(10) Patent No.: US 6,436,421 B1
(45) Date of Patent: Aug. 20, 2002

(54) PESTICIDE COMPOSITIONS

(75) Inventors: Frederick James Schindler, Fort Washington; Yili Guo; Gregory C. Pierce, both of Maple Glen; James Allen Quinn, North Wales, all of PA (US)

(73) Assignee: ?Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/032,135

(22) Filed: Feb. 27, 1998

Related U.S. Application Data
(60) Provisional application No. 60/038,134, filed on Mar. 3, 1997.

(51) Int. Cl.[7] ............................................... A01N 25/10
(52) U.S. Cl. ...................... 424/405; 424/407; 424/408; 424/409; 424/417; 424/419; 424/420; 504/190; 504/334; 504/352; 514/184; 514/242; 514/412; 514/465; 514/481; 514/483; 514/494; 514/499; 514/520; 514/535; 514/615; 514/617; 514/726
(58) Field of Search ..................... 424/405, 408, 424/409, 417, 420, 687, 407, 633, 635; 504/190, 334, 352; 514/184, 242, 465, 481, 483, 494, 499, 520, 563.5, 615, 617, 716, 726, 412

(56) References Cited

U.S. PATENT DOCUMENTS

| 132,543 A | * | 10/1872 | Smith ........................... 424/687 |
| 4,282,207 A | * | 8/1981 | Young et al. ................... 424/78 |
| 5,169,644 A | * | 12/1992 | Molls et al. ................... 424/497 |
| 5,342,646 A | * | 8/1994 | Reese et al. ................... 427/2.1 |
| 5,439,690 A | * | 8/1995 | Knight ........................ 424/687 |

FOREIGN PATENT DOCUMENTS

| DE | 28 04 563 A | | 2/1978 |
| DE | 42 29 460 A1 | | 9/1992 |
| JP | 52072789 | * | 6/1977 |
| JP | 08 119 813 A | | 5/1996 |

OTHER PUBLICATIONS

Kent Ed. 7th Edition p 619,620 Riegels's Handbook of Industrial Chem. p.'74.*
Fifra 1 p. 7 Fed Register 540/09–89–012 Oct. 1,1988.*

* cited by examiner

Primary Examiner—Neil S. Levy
(74) Attorney, Agent, or Firm—Thomas D. Rogerson

(57) ABSTRACT

The present invention relates to pesticide compositions. In particular, the present invention relates to pesticide compositions comprising a pesticide and a redispersible polymer and to a method for controlling agricultural pests by applying to the pest or the locus of the pest a pesticide composition comprising a pesticide and a redispersible polymer.

7 Claims, No Drawings

PESTICIDE COMPOSITIONS

This application claims the benefit of provisional application Ser. No. 60/038,134 filed on Mar. 3, 1997.

The present invention relates to pesticide compositions. In particular, the present invention relates to pesticide compositions comprising a pesticide and a redispersible polymer. The present invention also relates to a method for controlling agricultural pests by applying to the pest or the locus of the pest a pesticide composition comprising a pesticide and a redispersible polymer.

Compositions intended for the control of agricultural pests are typically applied by spraying a composition comprising the pesticide using water as a carrier liquid. For this reason, pesticide compositions are supplied to the grower in formulations which are intended to be dissolved or dispersed in water. These formulations may be liquid formulations such as aqueous solutions or emulsifiable concentrates or solid formulations such as wettable powders or granular formulations. Solid formulations have many advantages over liquid formulations in terms of cost, storage, and packaging, including disposal of packaging.

Biological efficacy of pesticides is influenced by many factors, particularly the residence time of the pesticide on the treated surface, which is often a plant leaf surface. A major factor influencing the residence time is the degree to which the pesticide resists wash-off by rain, that is, rainfastness. With liquid formulations, rainfastness may be improved by including ingredients in the formulation or adding such ingredients to the spray tank (tank mixing) that, during drying, provide a water-resistant bond between the pesticide and the substrate. For example, emulsified oil or water insoluble polymers prepared in emulsion have been used to improve liquid formulation rainfastness. One widely used material is a formulation comprising a carboxylated synthetic latex emulsion polymer, a primary aliphatic oxyalkylated alcohol, and water. This material has been shown to improve the efficacy of a variety of pesticides. However, because it is a liquid formulation, it cannot be used as a component of a solid pesticide formulation.

Solid formulations present a different set of competing problems when compared to liquid formulations. In order for solid formulations to readily disperse in water, water-resisting additives cannot be used in the formulation. In fact, high levels of water soluble dispersants are typically required so that the solid formulation will disperse in the spray tank. Although emulsified oil or water insoluble polymers prepared in emulsion have been used with liquid formulations or in tank mixes, none has been described that address the problem of improving rainfastness of solid formulations without requiring a separate tank mix additive. This is both inconvenient and problematic for the grower who desires to use a dry, solid pesticide formulation. Dry solid formulations are particularly important because they can be more easily stored, packaged, and transported than their liquid counterparts. Therefore, there is a continuing need for additives which are compatible with solid pesticide formulations.

We have discovered that redispersible polymers may be used as pesticide additives. Redispersible polymers are solid compositions which incorporate water insoluble polymers prepared in emulsion combined, prior to drying, with water soluble polymers. Such compositions are typically isolated by spray drying and the products are referred to as redispersible powders. The water soluble polymer is critical for redispersion of the water insoluble polymer. These polymers overcome many of the problems associated with the use of emulsion polymers as adjuvants in solid pesticide formulations. In addition, they provide a surprising increase in the efficacy of many pesticides and improved resistance to wash-off by rain.

Thus, this invention provides a pesticide composition, comprising:
(a) one or more pesticides; and
(b) one or more redispersible polymers comprising:
  (1) one or more water insoluble polymers prepared in emulsion; and
  (2) one or more water soluble polymers.

The composition may further comprise other ingredients to aid in dispersibility of the pesticide in water, modify surface tension of the spray, and promote adhesion of the water insoluble polymers.

The term "pesticide" means a chemical which is intended to mitigate a pest including insects, weeds, fungi, and related organisms. For purposes of this invention, a pesticide can also include viruses, bacteria, or other organisms which can control pests and which are found or can be modified to form a stable particle. The pesticide preferably comprises 5 to 90% by weight of the pesticide composition. The pesticide of the composition of this invention may be in the form of a pure active ingredient, a technical grade of the active ingredient, or an active ingredient formulated with one or more agronomically acceptable carriers. By "agronomically acceptable carrier" is meant any substance which can be used to aid the dispersion of the active ingredient in the composition in water without impairing the active ingredient's effectiveness and which by itself has no significant detrimental effect on the soil, equipment, desirable plants, or the agronomic environment. Pesticides in the form of particles are preferred. Most preferred are particles in the range of 0.1 to 20 microns in diameter.

The term "redispersible polymer" means a free-flowing dry powder comprising one or more water insoluble polymers and one or more water soluble polymers, produced by drying an emulsion polymer dispersion, that redisperses readily in water but, when dried a second time, forms a water resistant film. Redispersible polymers are well known in the art. See, for example, U.S. Pat. No. 3,784,648 (RE 28,780) (water insoluble synthetic resins with a water soluble condensation product of melamine and formaldehyde which contains sulfonate groups); U.S. Pat. No. 5,536,779 (polymer powder derived from unsaturated monomers and at least one added starch-degradation product); U.S. Pat. No. 5,519,084 (acrylic emulsion polymers and polyvinyl alcohol); DE 4,402,408 (unsaturated copolymers and post-added protective colloids); JP 7,053,730 (acrylic emulsion polymers and colloid prepared from sodium styrene sulfonate and a polymerizing emulsifying agent); EP 632096 (acrylic and vinyl emulsion polymers with amino functional polyvinyl alcohol); U.S. Pat. No. 5,252,704 (acrylic and vinyl emulsion polymers with polyvinyl pyrollidone); U.S. Pat. No. 5,225,478 (emulsion polymers of olefinically unsaturated monomers with water soluble metal salts of phenol-sulfonic acid/formaldehyde condensates); and EP 723975 (emulsion copolymers of styrene and alkyl(meth)acrylates with water soluble colloids).

Many redispersible polymers are two-stage emulsion polymers formed when a second-stage, water soluble polymer forms a "shell" or coating around a discreet domain or "core" of the first-stage, water insoluble polymer. Examples of such core-shell polymers are disclosed in U.S. Pat. Nos. 4,916,171 and 5,403,894. In these examples, the water soluble polymer is a copolymer of methacrylic acid that is neutralized with base. U.S. Pat. No. 4,876,313 also discloses the use of polyfunctional compounds to partially graft or bond the water soluble and water insoluble polymers.

One embodiment of this invention provides a composition comprising a pesticide, formulated as a wettable powder, a dust, or a dispersible granule, and a redispersible powder comprising one or more water insoluble polymers prepared in emulsion and one or more water soluble polymers, such as those disclosed in the above references.

Another embodiment of this invention provides a wettable powder, a dust, or dispersible granule pesticide formulation comprising one or more pesticides and one or more redispersible polymers wherein the formulation is prepared by a process comprising the steps of:

a) combining a dispersion of the pesticide in water with one or more water insoluble polymers formed in emulsion and one or more water soluble polymers and b) drying the combination.

Another embodiment of this invention provides a dry pesticide adjuvant comprising one or more redispersible polymers comprising:

(1) one or more water insoluble polymers prepared in emulsion; and (2) one or more water soluble polymers.

Still another embodiment of this invention provides a method of controlling a pest comprising applying to the pest, the locus of the pest, or a food source of the pest a pesticide composition comprising:

(a) one or more pesticides; and (b) a redispersible polymer comprising:

(1) one or more water insoluble polymers prepared in emulsion; and (2) one or more water soluble polymers.

Preferred water insoluble polymers are polymerized in emulsion and have an emulsion particle size of 0.1 to 5 microns. In order to obtain the proper balance of properties, preferred water insoluble polymers are selected from one or more homopolymers and copolymers independently comprising polymer units derived from: (1) one or more acrylic ester monomers; acrylamide or substituted acrylamides; styrene or substituted styrenes; butadiene; vinyl acetate or other vinyl esters; vinyl monomers such as vinyl chloride, vinylidene chloride, N-vinyl pyrolidone; acrylonitrile, and methacrylonitrile wherein the water insoluble polymer has a glass transition temperature between 0 and 60 degrees Celcius (° C.), preferably between 0 and 40° C. and (2) ethylene and vinyl esters wherein the water insoluble polymer has a glass transition temperature between −20 and 40° C. Acrylic ester monomers include, for example, methyl acrylate, ethyl acrylate, butyl acrylate, 2-ethylhexyl acrylate, decyl acrylate, methyl methacrylate, butyl methacrylate, hydroxyethyl methacrylate, and hydroxypropyl acrylate. The preferred water insoluble polymer comprises monomer units derived from 2-ethylhexyl acrylate, butyl acrylate, ethyl acrylate, methyl acrylate, methyl methacrylate, styrene, and vinyl acetate. When the water insoluble polymer comprises units derived from vinyl acetate, a more preferred form of the polymer has more than 3% of the vinyl acetate units hydrolyzed by addition of an inorganic base. The water insoluble polymer preferably comprises 5–80% by weight of the pesticide composition.

Preferred water soluble polymers are non-ionic polymers wherein the non-ionic polymer has a molecular weight greater than 2,000 amu such as, for example, polymers and copolymers comprising units derived from one or more of polyvinyl alcohol, methyl methacrylate, and methacrylic acid. Polyvinyl alcohol or partially hydrolyzed copolymers of vinyl esters, for example, vinyl acetate, are preferred non-ionic polymers. The water soluble polymer preferably comprises 1–40% by weight of the pesticide composition.

The compositions of this invention often benefit from the presence of added surfactant. One skilled in the art will recognize circumstances where surfactants are typically combined with the pesticide to be applied. We have found that in some cases, the combination of surfactant and redispersible polymer provides an increase in biological activity of the pesticide beyond that which would be expected based on the biological activity of the pesticide in the presence of either the surfactant or the redispersible polymer alone. One possible explanation for this phenomenon is that the redispersible polymer provides improved resistance to washoff to the pesticide/surfactant mixture. Surfactants that may be employed in combination with redispersible polymers include one or more of various nonionic, anionic, and amphoteric surfactants. Examples of nonionic surfactants which are useful include polyalkylene glycol ethers and condensation products of alkyl phenols, aliphatic alcohols, aliphatic amines, and fatty acids with ethylene oxide, propylene oxide or their mixtures such as the ethoxylated alkyl phenols or ethoxylated aryl and polyaryl phenols and carboxylic esters solubilized with a polyol or polyoxyethylene. Anionic surfactants include salts of alkyl aryl sulphonic acids, sulphated polyglycol ethers, salts of sulfosuccinic acid esters with hydrophobes such as 2-ethylhexanol, salts of phosphated polyglycol ethers, alkyl sarcosine salts, alkyl isethionate salts, and derivatives of taurine. Additional benefit is provided by surfactants that improve the adhesive character of the redispersible polymer. Most preferred are solid surfactants which can be dry blended with the pesticide/redispersible polymer composition. Examples of such surfactants include dioctyl sodium sulfosuccinate, sodium lauryl sulfate, and fatty acid amides of N-methyltaurine.

To further promote the formation of a film containing the pesticide on the surface to which the pesticide is applied, one or more additional film-forming aids may be added to the composition. Such aids include low molecular weight solids which are soluble in both water and in the polymer. Preferred film-forming aids include caprolactam and neopentyl glycol. Some solid surfactants, such as dioctyl sodium sulfosuccinate, may also serve as film-forming aids.

The compositions of this invention may be prepared in a variety of ways. One method is to mechanically combine the pesticide with the redispersible polymer, both components in the form of solids. This mixing process can range from as simple a procedure as physically blending the two solid materials together to as complex a process as blending the two components together with additional components and forming a granular material wherein the granular particles contain both components. Alternatively, the redispersible powder may be mixed with a dispersible granule forming a surface coating on the granule. The compositions can also be prepared by combining an aqueous dispersion of the pesticide component containing at least one of the water insoluble polymers with the water soluble polymer and then drying to solid form.

The redispersible polymer itself may also be added to the spray tank before or after addition of the pesticide.

For some applications, one or more pesticides may be combined in the compositions of the present invention, thereby providing additional advantages and effectiveness, including fewer total pesticide applications, than if the pesticides are applied separately. When mixtures of pesticides are employed, the relative proportions of each in the composition will depend upon the relative efficacy and the desired application rate of each pesticide with respect to the crops and/or weeds to be treated. Those skilled in the art will recognize that mixtures of pesticides may provide advantages such as a broader spectrum of activity than one pesticide used alone.

Examples of pesticides which can be combined in the compositions of the present invention include: (1) fungicides such as, for example, (a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts; (b) nitrophenol derivatives such as: dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate; (c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazolone-3,2,4-dichloro-6-(o-chloroanilino)-s-triazine, diethyl phthalimidophosphorothioate, 4-butyl-1,2,4-triazole, 5-amino-1-(bis(dimethylamino)phosphinyl)-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-(4,5-b)quinoxaline-2-thione (thioquinox), ethyl 1-(butylcarbamoyl)-2-benzimidazole carbamate (benomyl), 2-4'-(thiazolyl)benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinolozolin); 3-(3,5-dichlorophenyl)-N-(1-methylethyl)-2,4-dioxo-1-imidazolidinecarboxamide (iprodione); N-(3,5-dichlorophenyl)-1,2-dimethylcyclopropane-1,2-dicarboximide (procymidone), beta-(4-dichlorophenoxy)-alpha-(1,1-dimethylethyl)-1"H-1,2,4-triazole-1-ethanol (triadimenol); 1-(4-chlorophenoxy)-3,3-dimethyl-1-(1H-1,2,4-triazol-1-yl)-2-butanone (triadimefon); beta-(1,1'-biphenyl)-4-yloxyl)-alpha-(1,1-dimethylethyl)-1H-1,2,4-triazole-1-ethanol (bitertanol); 2,3-dichloro-N-(4-fluorophenyl)maleimide (fluoroimide); 1-(2-(2,4-dichlorophenyl)-4-propyl-1,3-dioxolan-2-ylmethyl)-1"H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha(phenyl)-alpha-(2,4-dichlorophenyl)-5-pyrimidinylmethanol (triarimol), cis-N-(1,1,2,2-tetrachloroethyl)thio)-4-cyclohexene-1,2-dicarboximide, 3-(2-(3,5-dimethyl-2-oxycyclohexyl)-2-hydroxy)glutarimide (cycloheximide), dehydroacetic acid, N-(1,1,2,2-tetrachloroethylthio)-3a,4,7,7-tetrahydrophthalimide (captafol), butyl-2-ethylamino-4-hydroxy-6-methylpyrimidine (ethirimol), acetate of 4-cyclodecyl-2,6-dimethyl-morpholine (dodemorph), 4-(3-(4-chlorophenyl)-3-(3,4-dimethoxyphenyl)acryloyl) morpholine (dimethomorph), thifluzamide, and 6-methyl-2-oxo-1,3-dithiolo(4,5-b)-quinoxaline (quinomethionate); (d) miscellaneous halogenated fungicides such as: tetrachloro-p-benzoquinone (chloranil), 2-3-dichoro-1,4-napththoquinone(dichlone), 1,4-dichloro-2,5-dimethoxybenzene(chloroneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, polychloronitrobenzenes such as pentachloronitrobenzene (PCNB), and tetrafluorodichloroacetone; (e) fungicidal antibiotics such as: griseofulvin, kasugamycin and streptomycin; (f) copper-based fungicides such as: copper hydroxide, cuprous oxide, basic cupric chloride, basic copper carbonate, copper terphthalate, copper naphthenate and Bordeaux mixture; and (g) miscellaneous fungicides such as: diphenyl, sulfone, dodecylguanidine acetate (dodine), aluminum tris-o-ethyl phosphonate (fosetylal), N-(2,6-dimethylphenyl)-N-(methoxyacetyl)alanine methyl ester(methoxyl) and other alkaline fungicides, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel containing compounds, calcium cyanamide, lime sulfur, 1,2-bis-(3,-methoxycarbony-2-thioureido)benzene (thiophanate-methyl), and 2-cyano-N-(ethylamino)carbonyl)-2-(methoxyimine)acetamide (cymoxanil); as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy)pyrimidin-4-yloxy)phenyl)-3-methoxyacrylate; benzo(1,2,3)thiadiazole-7-carbothioic acid S-methyl ester: propamocarb; imazalil; carbendazim; myclobutanil; fenbuconazole; tridemorph; pyrazophos; fenarimol; fenpiclonil; pyrimethanil; and tin fungicides; (2) herbicides, such as, (a) carboxylic acid derivatives, including benzoic acids and their salts; phenoxy and phenyl substituted carboxylic acids and their salts; and trichloroacetic acid and its salts; (b) carbamic acid derivatives, including ethyl N,N-di(n-propyl)thiolcarbamate and pronamide; (c) substituted ureas, (d) substituted triazines, (e) diphenyl ether derivatives such as oxyfluorfen and fluoroglycofen, (f) anilides such as propanil, (g) oxyphenoxy herbicides, (h) uracils, (i) nitriles, and (j) other organic herbicides such as dithiopy and, thiazopyr; and (3) insecticides, including acephate, acethion, acetoxon, aldicarb, aldoxycarb, aldrin, allethrin, allyxycarb, alpha-cypermethrin, amidithion, amitraz, amlure, anethol, azethion, azinphos-ethyl, azinphos-methyl, azocyclotin, bacillus thuringiensis, BCPE, bendiocarb, bensultap, benzoximate, benzyl acetate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chloropenozide, chloropropylate, chlorphoxim, chlorpyrifos, chlorpyrifos methyl, chlorthiophos, clofentezine, CPCBS, CPMC, crotoxyphos, crufomate, cryolite, cufraneb, cyanofenphos, cyanophos, cyanthoate, cyfluthrin, cyhexatin, cypermethrin, cyphenothrin, cyromazine, DAEP, DDT, DDVP, deltamethrin, demeton, demeton-S-methyl, demeton-O-methyl, demeton-S, demeton-S-methyl sulfoxid, demephion-O, demephion-S, dialifor, diazinon, dicapthon, dichlofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, d-trans allethrin, endosulfan, endothion, endrin, entice, EPBP, EPN, esfenvalerate, ethiofencarb, ethion, ethoate-methyl, ethoprop, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, flufenoxuron, fluvalinate, fonofos, formetanate hydrochloride, formothion, fosmethilan, fosthietan, furathiocarb, furethrin, grandlure, heptachlor, HETP, hexythiazox, hydramethylnon, hydroprene, IPSP, isazophos, isobenzan, isofenphos, isoprocarb, isoprothiolane, isothioate, isoxathion, jodfenphos, kinoprene, lead arsenate, leptophos, lethane, lindane, lythidathion, malathion, mazidox, mecarbam, mecarphon, menazon, mephosfolan, methamidophos, methidathion, methiocarb, methomyl, methoprene, methoxychlor, methoxyfenozide, methyl parathion, methyl phencapton, mevinphos, mexacarbate, MIPC, mirex, monocrotophos, MTMC, naled, nicotine, nonachlor, omethoate, ovex, oxamyl, oxydeprofs, oxydisulfoton, oxythioquinox, paraoxon, parathion, paris green, permethrin, perthane, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnell, rotenone, ryania, s-bioallethrin, salithion, schradan, sodium fluosilicate, sophamide, sulfotepp, sulprofos, tebufenozide, tefluthrin, temephos, TEPP, terbufos, tetrachlorvinphos, tetradifon, tetramethrin, tetrasul, thallium sulfate, thiocarboxime, thiocyclam hydrogenoxalate, thiometon, tolclofos-methyl, toxaphene, triazamate, triazophos, trichlorfon, trichloronate, triflumuron, trimethacarb, vamidothion, and xylylcarb.

The compositions of the present invention can be applied to plant foliage as aqueous sprays by methods commonly employed, such as conventional high-liter hydraulic sprays, low-liter sprays, air-blast, and aerial sprays. The dilution and rate of application will depend upon the type of equipment employed, the method and frequency of application desired, the pesticide application rate, and the pests to be controlled. Although the use of redispersible polymers reduces the need for other adjuvants, it may be desirable to include additional adjuvants in the spray tank, Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials,* and *McCutcheon's Functional Materials,* all published annually by McCutcheon Division of MC Publishing Company (New Jersey).

The compositions of the present invention can also be mixed with fertilizers or fertilizing materials before their application. In one type of solid fertilizing composition, particles of a fertilizer or fertilizing ingredients, such as ammonium sulfate, ammonium nitrate, or ammonium phosphate, can be coated with one or more of the compositions. The compositions and solid fertilizing material can also be admixed in mixing or blending equipment, or they can be incorporated with fertilizers in granular formulations. Any relative proportion of fertilizer can be used which is suitable for the crops and weeds to be treated. The compositions of the invention will commonly comprise from 5% to 50% of the fertilizing composition. These compositions provide fertilizing materials which promote the rapid growth of desired plants, and at the same time control pests.

The emulsion polymers used in the redispersible polymers of this invention may be prepared by addition polymerization of one or more ethylenically unsaturated monomers such as, for example, acrylic ester monomers including methyl acrylate, ethyl acrylate, butyl acrylate, 2-ethylhexyl acrylate, decyl acrylate, methyl methacrylate, butyl methacrylate, hydroxyethyl methacrylate, and hydroxypropyl acrylate; acrylamide or substituted acrylamides; styrene or substituted styrenes; butadiene; vinyl acetate or other vinyl esters; vinyl monomers such as vinyl chloride, vinylidene chloride, N-vinyl pyrolidone; and acrylonitrile or methacrylonitrile. Low levels of copolymerized ethylenically unsaturated acid monomers such as, for example, 0.1%–7, by weight, based on the weight of the emulsion-polymerized polymer, acrylic acid, methacrylic acid, crotonic acid, phosphoethyl methacrylate, 2-acrylamido-2-methyl-1-propanesulfonic acid, sodium vinyl sulfonate, itaconic acid, fumaric acid, maleic acid, monomethyl itaconate, monomethyl fumarate, monobutyl fumarate, and maleic anhydride may be used. Preferred acrylic copolymers with styrene contain from 10% to 60% styrene based on the total weight of the polymer. The polymers may be single-stage or multi-stage polymers.

The emulsion polymerization techniques used to prepare redispersible emulsion polymers are well known in the art. See, for example, U.S. Pat. No. 5,346,954. Multi-stage polymers are well known in the art and are disclosed, for example, in U.S. Pat. Nos. 4,325,856, 4,654,397, and 4,814,373. Surfactants such as, for example, anionic and/or non-ionic emulsifiers such as alkali or ammonium alkyl sulfates, alkyl sulfonic acids, fatty acids, and oxyethylated alkyl phenols may be used in these types of polymerizations. The amount of surfactant used is usually 0.1% to 6% by weight, based on the weight of total monomer. Depending on the specific redispersible polymer to be prepared, either thermal or redox initiation processes may be used. Conventional free radical initiators may be used such as, for example, hydrogen peroxide, t-butyl hydroperoxide, ammonium and alkali persulfates, typically at levels of 0.05% to 3% by weight, based on the weight of total monomer. Redox systems using the same initiators coupled with a suitable reductant such as, for example, isoascorbic acid and sodium bisulfite may be used at similar levels. The particular procedure to be used is dependent upon the particular polymer being prepared; not all conditions work in all cases. However, one skilled in the art can easily determine the appropriate conditions without undue experimentation.

Procedure for Preparation of a Redispersible Polymer

The following procedure describes the preparation of the redispersible polymer designated as Powder III in the following examples.

A 5 liter, 4-necked round bottom flask equipped with a mechanical stirrer, thermocouple, condenser, and nitrogen sparge was charged with (a) 3000 grams of a 55 percent, by weight of polymer solids, aqueous emulsion of an emulsion copolymer having a monomer composition of 19.1 percent, by weight, butyl acrylate, 80.65 grams of vinylacetate, and 0.25 percent, by wight, of sodium vinylsulfonate, and (b) 363 grams of an aqueous polyvinyl alcohol solution (17.3% by weight, Vinol™203, Air Products Company). To the mixture was then added 150 grams of calcium hydroxide in 1200 grams of water. The mixture was then heated at 85° C. for 2 hours. The hydrolyzed product was then cooled and filtered through a 100 mesh screen.

The filtered hydrolyzed product was spray-dried using a Bowen Model BLSA laboratory spray dryer. Inlet air temperature was adjusted to 122° C. and outlet air temperature was 57° C. as regulated by the feed rate. The resulting product had a residual moisture level of less than 4% and was a free-flowing white powder which readily redispersed in water.

Procedure for Evaluating Effect of Polymer Additives on Resistance of Pesticide Formulations to Wash-Off by Water One method to evaluate the efficacy of a pesticide adjuvant is to measure its affect on the ability of the pesticide composition to resist wash-off from a surface. One skilled in the art will recognize that a pesticide which remains on the surface of a plant will be expected to have increased efficacy.

A suspension of the pesticide formulation was prepared by adding a premix of water and surfactant, with and without the polymer additives, followed by vigorous shaking of the mixtures by hand. Pieces of Parafilm™M laboratory film, a very soft, flexible, and hydrophobic film, were taped to plastic petrie dishes. The suspensions were sprayed with an automated sprayer as the petrie dishes with attached film were moved at a standard rate below the sprayer. The spray residues were allowed to dry, and a second application of spray was applied. One set of films was exposed, at an inclination of 45 degrees, to approximately 25 mm of water applied by a spray bar (equipped with TX-4 cone-type spray nozzles) that moved back and forth over the samples for a period of about 1 hour. The exposed films were allowed to dry. Another set of films was not exposed to water.

Infra-red spectra of the films were obtained by an Attenuated Total Reflection (ATR) technique. The films were pressed against a Zinc Selenide crystal that had been cleaned previously with methanol. Spectra were recorded with a Spectratech Allied Systems Fourier Transform Infra-Red Spectrometer, and stored in a computer. Peaks associated with pesticide residue were identified by inspection and peak areas were calculated by computer (Pesticide Peak Area, "PA"). A corresponding area for a Parafilm™ peak as similar as possible in peak location and size (in the same spectrum) was calculated (Film Peak Area, "FA"). Similar calculations were conducted for a spectrum of the film which had not been sprayed with pesticide, giving corresponding reference peak areas "RPA" and "RFA". A measure of the pesticide on the surface "P" was derived from the following calculation:

$$P = PA/FA - RPA/RFA.$$

A relative measure of the amount of pesticide remaining after the above exposure to water was then derived from the following calculation:

$$\text{Relative Amount Remaining} = \frac{100(PA/FA - RPA/RFA) \text{ for exposed film}}{(PA/FA - RPA/RFA) \text{ for unexposed film}}.$$

Although the intensity of spectral peaks recorded with the ATR technique are very dependent on details of contact with the film, by obtaining a ratio of the pesticide peak to the film peak in the same spectral recording, different spectra can be compared with details of contact being compensated for, since they will have similar effects on the intensity of the pesticide absorption and the film absorption. The intensity of the pesticide peak relative to the film peak will depend on the degree of coverage of the film by the pesticide. To maximize coverage, the spraying was conducted twice. Furthermore, a wetting agent (surfactant) was included in the premix to promote wetting of the film by the spray droplets. Since exposure to water can result in re-distribution of the pesticide as well as wash-off of the pesticide, the measure of the amount remaining is only relative. When there is little wash-off, the redistribution effect can make the above ratio greater than 100.

The following table shows details of the spray mixes and spraying conditions, as well as the IR bands for pesticide and Parafilm (reference) used for measuring the amount of pesticide present. In all cases, a measured amount of pesticide was mixed with 270 grams of deionized water and 30 grams of 0.5% Silwet L-77 surfactant. This premix was divided into 50 gram portions. One portion was sprayed without adding polymer. For mixes containing polymer, 66.6 milligrams powder polymer or 1.32 g of a 5% solids dilution of the emulsion polymer were added to the 50 grams of premix.

The following pesticide types and pesticides were evaluated: (1) fungicides; mancozeb 80% wettable powder (WP), maneb 80% WP, ziram 76% dispersible granule (DG), chlorothalonil 82.5% DG, copper hydroxide 77% WP, myclobutanil 40% WP, fenbuconazole 75% WP, captan 50% WP, (2) insecticides; carbaryl flowable (FLO), cartap 50% WP, carbofuran 4 pound per gallon FLO, tebufenozide 70% WP, dicofol 50% WP, dinocap WP; and (3) herbicides; propanil 80% DG, and oxyfluorfen 75% FLO.

| Pesticide | Grams Used in Premix | Spray Condition | Infrared Bands Used | |
|---|---|---|---|---|
| | | | Pesticide | Parafilm |
| mancozeb | 2.4 | A | 1287 | 1231 |
| maneb | 2.4 | A | 1287 | 1231 |
| ziram | 2.4 | A | 1518 | 1231 |
| chlorothalonil | 2.4 | A | 1549 | 1231 |
| copper hydroxide | 2.4 | A | 698 | 725 |
| myclobutanil | 2.4 | A | 1096 | 1231 |
| fenbuconazole | 2.4 | A | 1030 | 1231 |
| captan | 2.4 | A | 1015 | 1231 |
| carbaryl | 4.2 | A | 1115 | 725 |
| cartap | 3.8 | A | 1675 | 1470 |
| carbofuran | 4.3 | A | 1717 | 1470 |
| tebufenozide | 2.7 | B | 1648 | 1470 |
| dicofol | 3.8 | A | 768 | 725 |
| dinocap | 9.5 | A | 1581 | 1231 |
| propanil | 2.4 | B | 1546 | 1470 |
| oxyfluorfen | 2.5 | B | 1081 | 1231 |

Spraying condition A:
  TX-2 nozzle 12 inches above laboratory film.
  58 psi (delivers 150 cc/minute).
  Laboratory film moves at 1 mile/hour.

Spraying condition B:
  Fan nozzle 14 inches above laboratory film.
  29 psi (Spray 15 cc with two passes over laboratory film at a rate to give 25 gallons/acre).

Three different solid redispersible polymers were evaluated: Powder I, an ethylene/vinyl acetate copolymer with polyvinyl alcohol (Airflex™ RP-245 redispersible powder from Air Products Company; a cement modifier); Powder II a styrene/butyl acrylate copolymer with polyvinyl alcohol (Vinnapas™ LL-564 redispersible powder from Wacker Chemical Company; a cement modifier); and Powder III, a redispersible powder prepared as described in the synthesis example above.

One aqueous emulsion polymer of a type used as a spray tank additive was included for reference: EmulsionIV, a styrene butadiene copolymer with surfactant (Rovene™ 4150 emulsion from Mallard Creek Polymers Company, an adhesive for carpet backing).

"% AI Retained After One Inch ""Spray-Bar"" Rain"

| Pesticide | No Polymer | | Powder I | | Powder II | | Powder III | | Emulsion IV | |
|---|---|---|---|---|---|---|---|---|---|---|
| | M | SD | M | SD | M | SD | M | SD | M | SD |
| mancozeb | 21 | 3 | 76 | 33 | 124 | 23 | 77 | 6 | 107 | 4 |
| maneb | 16 | 2 | 76 | 8 | 108 | 1 | 86 | 13 | 103 | 6 |
| ziram | 60 | 3 | 88 | 5 | 111 | 5 | 94 | 11 | 104 | 12 |
| chlorothalonil | 2 | | 16 | 1 | 54 | 6 | 4 | 4 | 12 | 4 |
| copper hydroxide | 20 | 23 | 22 | 19 | 80 | 36 | 21 | 23 | 11 | |
| myclobutanil | 13 | 2 | 56 | 2 | 77 | 11 | 44 | 25 | 74 | 3 |
| fenbuconazole | 9 | 8 | 63 | 16 | 82 | 1 | 48 | 16 | 83 | 3 |
| captan | 41 | 8 | 75 | 12 | 68 | 9 | 51 | 11 | 69 | 11 |
| carbaryl | 25 | 1 | 31 | 3 | 32 | 9 | 27 | 5 | 40 | 7 |
| cartap | 4 | 1 | 5 | 6 | 8 | 2 | 8 | 2 | 3 | 1 |
| carbofuran | 3 | 1 | 39 | 1 | 23 | 1 | 16 | 2 | 9 | 1 |
| tebufenozide | 40 | 18 | 71 | 23 | 67 | 14 | 40 | 25 | 59 | 9 |
| dicofol | 18 | 1 | 76 | 12 | 62 | 1 | 62 | 13 | 95 | 27 |
| dinocap | 3 | <1 | 49 | 24 | 47 | 17 | 19 | 4 | 40 | 6 |
| propanil | 9 | | 38 | | 27 | | 21 | | 18 | |
| oxyfluorfen | 17 | 1 | 66 | 10 | 137 | 52 | 55 | 1 | 152 | 30 |

M = mean
SD = standard deviation

These data indicate that the redispersible polymers perform as well as the emulsion polymer.

Evaluation of Disease Control on Grape and Peanut Using Mancozeb Fungicide

For grapes, single plant plots with three replicates/treatment were treated at seven day intervals, with a total of seven applications. Treatments were water-based spray mixtures of mancozeb with or without polymer additives added to the water shortly before spraying. The mixtures were applied with a backpack sprayer using carbon dioxide pressure atomization (45 psi) with a boom having three D3 (Cone) nozzles, at a rate of 640 liters/hectare. The treatments included a control with no fungicide applied, a full rate of mancozeb without additive (2.8 kg active ingredient/hectare), and a half rate of mancozeb (1.4 kg active ingredient/hectare) with or without additives. The polymer additives were used at ⅓ kg. of additive solids/kg. of active ingredient. The mancozeb formulation was a wettable powder with 75% active ingredient.

Assessments of percent infection (of grape downy mildew caused by *Plasmopara viticola*) of foliage were made 7 days after treatment # 7 (7DAT#7). These assessments are tabulated below. Data were analyzed by Duncan's multiple range test, using P=0.05. (means not having a common letter are significantly different at a probability of 95%).

Peanuts were evaluated the same as grapes except that the plots were 1 meter×5 meter (1 row), with 4 replicates per treatment, there were 9 applications, the boom had five D2 (C45) nozzles, the full rate of mancozeb was 1.6 kg active ingredient/hectare, the final assessment was 23 days after treatment #9 (23DAT#9), and the predominant disease at this time was *Cercospora arachidicola* (Early Leaf Spot).

Three different solid redispersible powders were evaluated; Powders I and II from the previous example and powder V, an all acrylic copolymer (Drycryl™DP-2904 redispersible powder, a cement modifier of the Rohm and Haas Company). Three different emulsion polymers were evaluated for comparison; Emulsion IV from the previous example; Emulsion VI, a poly(vinylacetate) emulsion (Rovace™ 117 emulsion from the Rohm and Haas Company, used as a general purpose adhesive component); and Emulsion VII, an acrylic emulsion polymer (Rhoplex™ 2438 emulsion from the Rohm and Haas Company, a component of elastomeric wall coatings).

In several of the evaluations, a surfactant was added to the spray mixture. When used, the surfactant was a solid powder of 90% dioctyl sodium sulfosuccinate and 10% sodium benzoate (Aerosol® OTB surfactant from Cytec Company).

| Results from Grape and Peanut Field Tests Comparing Mancozeb at Half Rate with or without Additives | | | | |
|---|---|---|---|---|
| Mancozeb Use Rate | Polymer Additive | urfactant Additive | Infection on Peanut 23DAT#9 | Infection on Grape 7DAT#7 |
| None | None | No | 68.8 a | 91.7 a |
| Full | None | No | 27.5 cd | 41.7 cd |
| Half | None | No | 41.3 b | 63.3 b |
| Half | Emulsion VI | No | 22.5 ef | 43.3 cd |
| Half | Emulsion VI | Yes | 13.8 h | 31.7 fg |
| Half | Powder II | No | 32.5 c | 43.3 cd |
| Half | Powder II | Yes | 17.5 g | 28.3 g |
| Half | Powder V | No | 22.5 ef | 46.7 c |
| Half | Emulsion IV | No | 25.0 de | 38.3 de |
| Half | Emulsion VII | No | 21.3 f | 41.7 cd |
| Half | Powder I | No | 23.8 ef | 46.7 c |

The results of these evaluations indicate that all of the polymer additives significantly improved efficacy (decreased infection) of the half rate of mancozeb, giving efficacy as good as the full rate with out additives. A further significant improvement of efficacy resulted when surfactant was used in addition to polymer. The improvement in efficacy with redispersible polymers of different compositions was similar to that for two of the emulsion polymers (Emulsions VI and VII), and almost as good as for the other emulsion polymer (Emulsion IV).

These data demonstrate the effect of added surfactant on efficacy of mancozeb in both the presence and absence of a redispersible polymer adjuvant. The data indicate that at an appropriate level, the surfactant provides an increase in efficacy.

Evaluation of Beet Armyworm Control on Rice Using Tebufenozide

Rice plants grown in pots were sprayed with one of two different versions of a 300 parts per million (based on active ingredient level) suspension of tebufenozide in water. In one version, the tebufenozide was supplied as Mimic® 10 W insecticide, a wettable powder, from Rohm and Haas Company. In the second version, approximately 30% by weight of the carrier in the Mimic® 10 W insecticide was replaced with Powder V from the above examples and approximately 10% by weight of the clay carrier was replaced by Aerosol®OTB surfactant. One portion of each of the sprayed plant samples was subjected to approximately 25 millimeters of water applied by a spray bar to simulate rain. The plants were cut and fed to Beet Armyworm larvae. Percent mortality was then evaluated.

| | Beet Armyworm Mortality (%) | |
|---|---|---|
| | Without Rain | With Rain |
| Tebufenozide | 90 | 28 |
| Tebufenozide with Powder V | 100 | 65 |

Evaluation of Beet Armyworm Control Under Field Conditions

Each of two different plots of Chinese kale grown under typical field conditions was treated with one of the two tebufenozide formulations described above at an application rate of 300 g of tebufenozide per hectare in 750 liters of water per hectare. The percent beet armyworm mortality in each plot was compared to an untreated control plot.

|  | Beet Armyworm Control (%) |
|---|---|
| Tebufenozide | 35 |
| Tebufenozide with Powder V | 67 |

These data indicate that the redispersible polymer provides pesticide compositions with increased efficacy compared to an identical composition without the polymer

We claim:

1. A solid pesticide composition, comprising:
(a) 5 to 90% by weight one or more pesticides selected from the group consisting of:
(1) fungicides selected from the group consisting of;
(i) ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts
(ii) dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate;
(iii) N-trichloromethylthiotetrahydrophthalimide (captan), N-trichloromethylthiophthalimide (folpet), 2-heptadecyl-2-imidazole acetate (glyodine), 2-octylisothiazolone-3,2,4-dichloro-6-(o-chloroanilino)-s-triazine, diethyl phthalimidophosphorothioate, 4-butyl-1,2,4-triazole, 5-amino-1-(bis(dimethylamino) phosphinyl)-3-phenyl-1,2,4-triazole, 5-ethoxy-3-trichloromethyl-1,2,4-thiadiazole, 2,3-dicyano-1,4-dithiaanthraquinone (dithianon), 1,3-dithiolo-(4,5-b)quinoxaline-2-thione (thioquinox), ethyl 1-(butylcarbamoyl)-2-benzimidazole carbamate (benomyl), 2-4'-(thiazolyl)benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinolozolin); 3-(3,5-dichlorophenyl)-N-(1-methylethyl)-2,4-dioxo-1-imidazolidinecarboxamide (iprodione); N-(3,5-dichlorophenyl)-1,2-dimethylcyclopropane-1,2-dicarboximide (procymidone); beta-(4-dichlorophenoxy)-alpha-(1,1-dimethylethyl)-1"H-1,2,4-triazole-1-ethanol (triadimenol); 1-(4-chlorophenoxy)-3,3-dimethyl-1-(1H-1,2,4-triazol-1-yl)-2-butanone (triadimefon); beta-(1,1'-biphenyl)-4-yloxyl)-alpha-(1,1-dimethylethyl)-1H-1,2,4-triazole-1-ethanol (bitertanol); 2,3-dichloro-N-(4-fluorophenyl)maleimide (fluoroimide); 1-(2-(2,4-dichlorophenyl)-4 -propyl-1,3-dioxolan-2-ylmethyl)-1H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha (phenyl)-alpha-(2,4-dichlorophenyl)-5-pyrimidinylmethanol (triarimol), cis-N-(1,1,2,2-tetrachloroethyl)thio)-4-cyclohexene-1,2-dicarboximide, 3-(2-(3,5-dimethyl-2-oxycyclohexyl)-2-hydroxy)glutarimide (cycloheximide), dehydroacetic acid, N-(1,1,2,2-tetrachloroethylthio)-3a,4,7,7-tetrahydrophthalimide (captafol), butyl-2-ethylamino-4-hydroxy-6-methylpyrimidine (ethirimol), acetate of 4-cyclodecyl-2,6-dimethylmorpholine (dodemorph), 4-(3-(4-chlorophenyl)-3-(3,4-dimethoxyphenyl)acryloyl)morpholine (dimethomorph), thifluzamide, and 6-methyl-2-oxo-1,3-dithiolo(4,5-b)-quinoxaline (quinomethionate);
(iv) tetrachloro-p-benzoquinone (chloranil), 2-3-dichoro-1,4-napththoquinone (dichlone), 1,4-dichloro-2,5-dimethoxybenzene (chloroneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, pentachloronitrobenzene (PCNB) and related polychloronitrobenzenes, and tetrafluorodichloroacetone;
(v) griseofulvin, kasugamycin and streptomycin;
(vi) copper hydroxide, cuprous oxide, basic cupric chloride, basic copper carbonate, copper terphthalate, copper naphthenate and Bordeaux mixture; and
(vii) diphenyl sulfone, dodecylguanidine acetate (dodine), aluminum tris-o-ethyl phosphonate (fosetylal), N-(2,6-dimethylphenyl)-N-(methoxyacetyl)alanine methyl ester(methoxyl) and other alkaline fungicides, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel containing compounds, calcium cyanamide, lime sulfur, 1,2-bis-(3,-methoxycarbony-2-thioureido) benzene (thiophanate-methyl), and 2-cyano-N-(ethylamino)carbonyl)-2-(methoxyimine) acetamide (cymoxanil); furalaxyl, cyprofuram, ofurace, benalaxyl, oxadixyl, and related acylalanines; fluazinam, flumetover, phenylbenzamide, amino acid, methyl (E)-2-(2-(6-(2-cyanophenoxy) pyrimidin-4-yloxy)phenyl)-3-methoxyacrylate; benzo(1,2,3)thiadiazole-7-carbothioic acid S-methyl ester; propamocarb; imazalil; carbendazim; myclobutanil; fenbuconazole; tridemorph; pyrazophos; fenarimol; fenpiclonil; pyrimethanil; and tin fungicides;
(2) herbicides selected from the group consisting of;
(i) benzoic acids and their salts; phenoxy and phenyl substituted carboxylic acids and their salts; and trichloroacetic acid and its salts;
(ii) ethyl N,N-di(n-propyl)thiolcarbamate and pronamide;
(iii) substituted ureas;
(iv) substituted triazines;
(v) diphenyl ethers;
(vi) anilides;

(vii) oxyphenoxy herbicides;
(viii) uracils;
(ix) nitriles, and
(x) dithiopy and thiazopyr; and
(3) insecticides selected from the group consisting of acephate, acethion, acetoxon, aldicarb, aldoxycarb, aldrin, allethrin, allyxycarb, alpha-cypermethrin, amidithion, amitraz, amlure, anethol, azethion, azinphos-ethyl, azinphos-methyl, azocyclotin, bacillus thuringiensis, BCPE, bendiocarb, bensultap, benzoximate, benzyl acetate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chloropenozide, chloropropylate, chlorphoxim, chlorpyrifos, chlorpyrifos methyl, chlorthiophos, clofentezine, CPCBS, CPMC, crotoxyphos, crufomate, cryolite, cufraneb, cyanofenphos, cyanophos, cyanthoate, cyfluthrin, cyhexatin, cypermethrin, cyphenothrin, cyromazine, DAEP, DDT, DDVP, deltamethrin, demeton, demeton-S-methyl, demeton-O-methyl, demeton-S, demeton-S-methyl sulfoxid, demephion-O, demephion-S, dialifor, diazinon, dicapthon, dichlofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, d-trans allethrin, endosulfan, endothion, endrin, entice, EPBP, EPN, esfenvalerate, ethiofencarb, ethion, ethoate-methyl, ethoprop, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, flufenoxuron, fluvalinate, fonofos, formetanate hydrochloride, formothion, fosmethilan, fosthietan, furathiocarb, furethrin, grandlure, heptachlor, HETP, hexythiazox, hydramethylnon, hydroprene, IPSP, isazophos, isobenzan, isofenphos, isoprocarb, isoprothiolane, isothioate, isoxathion, jodfenphos, kinoprene, lead arsenate, leptophos, lethane, lindane, lythidathion, malathion, mazidox, mecarbam, mecarphon, menazon, mephosfolan, methamidophos, methidathion, methiocarb, methomyl, methoprene, methoxychlor, methoxyfenozide, methyl parathion, methyl phencapton, mevinphos, mexacarbate, MIPC, mirex, monocrotophos, MTMC, naled, nicotine, nonachlor, omethoate, ovex, oxamyl, oxydeprofs, oxydisulfoton, oxythioquinox, paraoxon, parathion, paris green, permethrin, perthane, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnell, rotenone, ryania, s-bioallethrin, salithion, schradan, sodium fluosilicate, sophamide, sulfotepp, sulprofos, tebufenozide, tefluthrin, temephos, TEPP, terbufos, tetrachlorvinphos, tetradifon, tetramethrin, tetrasul, thallium sulfate, thiocarboxime, thiocyclam hydrogenoxalate, thiometon, tolclofos-methyl, toxaphene, triazamate, triazophos, trichlorfon, trichloronate, triflumuron, trimethacarb, vamidothion, and xylylcarb;

(b) one or more redispersible polymers comprising:
(1) 5–80% by weight of the composition of one or more water insoluble polymers selected from one or more homopolymers and copolymers independently comprising polymer units derived from: (1) one or more acrylic ester monomers; acrylamide or substituted acrylamides; styrene or substituted styrenes; butadiene; vinyl acetate or other vinyl esters; vinyl chloride, vinylidene chloride, N-vinyl pyrolidone or related vinyl monomers; acrylonitrile, and methacrylonitrile wherein the water insoluble polymer has a glass transition temperature between 0 and 60 degrees Celcius (° C.) and (2) ethylene and vinyl esters wherein the water insoluble polymer has a glass transition temperature between –20 and 40° C.; and
(2) 1–40% by weight of the composition of one or more water soluble polymers selected from non-ionic polymers comprising, polymers and copolymers comprising units derived from one or more of polyvinyl alcohol, partially hydrolyzed copolymers of vinyl esters, methyl methacrylate, and methacrylic acid wherein the non-ionic polymer has a molecular weight greater than 2,000 amu.

2. The pesticide composition of claim 1 wherein the composition disperses in water to particles less than 40 microns in size.

3. The composition of claim 1 wherein the water insoluble polymer is selected from one or more homopolymers and copolymers independently comprising polymer units derived from one or more of 2-ethylhexyl acrylate, butyl acrylate, ethyl acrylate, methyl acrylate, and vinyl acetate wherein the water insoluble polymer has a glass transition temperature between 0 and 60 degrees C.

4. The composition of claim 3 herein more than 3 percent of any units derived from vinyl acetate which are present have been hydrolyzed.

5. The composition of claim 1 wherein the pesticide is selected from the group consisting of wettable powders and dispersible granules.

6. The composition of claim 1 wherein the pesticide is selected from the group consisting of mancozeb, maneb, ziram, chlorothalonil, copper hydroxide, myclobutanil, fenbuconazole, captan, carbaryl, cartap, carbofuran, tebufenozide, dicofol, dinocap; propanil, and oxyfluorfen.

7. A solid composition that disperses in water to particles smaller than 40 microns comprising:
a) 5 to 90% by weight of at least one pesticide selected from the group consisting of:
(1) fungicides selected from the group consisting of;
(i) ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3,5-2H-tetrahydrothiadiazine-2-thione (dazomet); and mixtures of these and mixtures with copper salts (ii) dinitro-(1-methylheptyl) phenyl crotonate (dinocap), 2-sec-butyl-4,6-dinitrophenyl-3,3-dimethylacrylate (binapacryl), and 2-sec-butyl-4,6-dinitrophenyl isopropyl carbonate;

(iii) N-trichloromethylthiotetrahydrophthalimide (captan), N-trichloromethylthiophthalimide (folpet), 2-heptadecyl-2-imidazole acetate (glyodine), 2-octylisothiazolone-3,2,4-dichloro-6-(o-chloroanilino)-s-triazine, diethyl phthalimidophosphorothioate, 4-butyl-1,2,4-triazole, 5-amino-1-(bis(dimethylamino) phosphinyl)-3-phenyl-1,2,4-triazole, 5-ethoxy-3-trichloromethyl-1,2,4-thiadiazole, 2,3-dicyano-1,4'-dithiaanthraquinone (dithianon), 1,3-dithiolo-(4,5-b)quinoxaline-2-thione (thioquinox), ethyl 1-(butylcarbamoyl)-2-benzimidazole carbamate (benomyl), 2-4'-(thiazolyl)benzimidazole (thiabendazole), 4-(2-chlorophenylhydrazono)-3-methyl-5-isoxazolone, 3-(3,5-dichlorophenyl)-5-ethenyl-5-methyl-2,4-oxazolidinedione (vinolozolin); 3-(3,5-dichlorophenyl)-N-(1-methylethyl)-2,4-dioxo-1-imidazolidinecarboxamide (iprodione); N-(3,5-dichlorophenyl)-1,2-dimethylcyclopropane-1,2-dicarboximide (procymidone); beta-(4-dichlorophenoxy)-alpha-(1,1-dimethylethyl)-1"H-1,2,4-triazole-1-ethanol (triadimenol); 1-(4-chlorophenoxy)-3,3-dimethyl-1-(1H-1,2,4-triazol-1-yl)-2-butanone (triadimefon); beta-(1,1'-biphenyl)-4-yloxyl)-alpha-(1,1-dimethylethyl)-1H-1,2,4-triazole-1-ethanol (bitertanol); 2,3-dichloro-N-(4-fluorophenyl)maleimide (fluoroimide); 1-(2-(2,4-dichlorophenyl)-4-propyl-1,3-dioxolan-2-ylmethyl)-1H-1,2,4-triazole; pyridine-2-thiol-1-oxide, 8-hydroxyquinoline sulfate and metal salts thereof; 2,3-dihydro-5-carboxanilido-6-methyl-1,4-oxathiin-4,4-dioxide, 2,3-dihydro-5-carboxanilido-6-methyl-1,4-oxathiin, alpha (phenyl)-alpha-(2,4-dichlorophenyl)-5-pyrimidinylmethanol (triarimol), cis-N-(1,1,2,2-tetrachloroethyl)thio)-4-cyclohexene-1,2-dicarboximide, 3-(2-(3,5-dimethyl-2-oxycyclohexyl)-2-hydroxy)glutarimide (cycloheximide), dehydroacetic acid, N-(1,1,2,2-tetrachloroethylthio)-3a,4,7,7-tetrahydrophthalimide (captafol), butyl-2-ethylamino-4-hydroxy-6-methylpyrimidine (ethirimol), acetate of 4-cyclodecyl-2,6-dimethyl-morpholine (dodemorph), 4-(3-(4-chlorophenyl)-3-(3,4-dimethoxyphenyl)acryloyl)morpholine (dimethomorph), thifluzamide, and 6-methyl-2-oxo-1,3-dithiolo(4,5-b)-quinoxaline (quinomethionate);

(iv) tetrachloro-p-benzoquinone (chloranil), 2-3-dichoro-1,4-napththoquinone (dichlone), 1,4-dichloro-2,5-dimethoxybenzene (chloroneb), 3,5,6-trichloro-o-anisic acid (tricamba), 2,4,5,6-tetrachloroisophthalonitril (TCPN), 2,6-dichloro-4-nitroaniline (dichloran), 2-chloro-1-nitropropane, pentachloronitrobenzene (PCNB) and related polychloronitrobenzenes, and tetrafluorodichloroacetone;

(v) griseofulvin, kasugamycin and streptomycin;

(vi) copper hydroxide, cuprous oxide, basic cupric chloride, basic copper carbonate, copper terphthalate, copper naphthenate and Bordeaux mixture; and (vii) diphenyl sulfone, dodecylguanidine acetate (dodine), aluminum tris-o-ethyl phosphonate (fosetylal), N-(2,6-dimethylphenyl)-N-(methoxyacetyl)alanine methyl ester(methoxyl) and other alkaline fungicides, phenylmercuric acetate, N-ethylmercuri-1,2,3,6-tetrahydro-3,6-endomethano-3,4,5,6,7,7-hexachlorophthalimide, phenylmercuric monoethanol ammonium lactate, p-dimethylaminobenzene sodium sulfonate, methyl isothiocyanate, 1-thiocyano-2,4-dinitrobenzene, 1-phenylthiosemicarbazide, nickel containing compounds, calcium cyanamide, lime sulfur, 1,2-bis-(3,-methoxycarbony-2-thioureido) benzene (thiophanate-methyl), and 2-cyano-N-(ethylamino)carbonyl)-2-(methoxyimine) acetamide (cymoxanil); furalaxyl, cyprofuram, ofurace, benalaxyl, oxadixyl, and related acylalanines; fluazinam, flumetover, phenylbenzamide, amino acid, methyl (E)-2-(2-(6-(2-cyanophenoxy) pyrimidin-4-yloxy)phenyl)-3-methoxyacrylate; benzo(1,2,3)thiadiazole-7-carbothioic acid S-methyl ester; propamocarb; imazalil; carbendazim; myclobutanil; fenbuconazole; tridemorph; pyrazophos; fenarimol; fenpiclonil; pyrimethanil; and tin fungicides;

(2) herbicides selected from the group consisting of;
  (i) benzoic acids and their salts; phenoxy and phenyl substituted carboxylic acids and their salts; and trichloroacetic acid and its salts;
  (ii) ethyl N,N-di(n-propyl)thiolcarbamate and pronamide;
  (iii) substituted ureas;
  (iv) substituted triazines;
  (v) diphenyl ethers;
  (vi) anilides;
  (vii) oxyphenoxy herbicides;
  (viii) uracils;
  (ix) nitriles, and
  (x) dithiopy and thiazopyr; and (3) insecticides selected from the group consisting of acephate, acethion, acetoxon, aldicarb, aldoxycarb, aldrin, allethrin, allyxycarb, alpha-cypermethrin, amidithion, amitraz, amlure, anethol, azethion, azinphos-ethyl, azinphos-methyl, azocyclotin, bacillus thuringiensis, BCPE, bendiocarb, bensultap, benzoximate, benzyl acetate, benzyl benzoate, BHC, bifenthrin, binapacryl, bomyl, BPMC, bromophos, bromophos-ethyl, bromopropylate, bufencarb, buprofezin, butacarb, butocarboxim, butonate, butoxycarboxim, calcium arsenate, carbaryl, carbofuran, carbophenothion, carbosulfan, cartap, chlordane, chlordecone, chlordimeform, chlorfenethol, chlorfenson, chlorfensulphide, chlorfenvinphos, chlormephos, chlorobenzilate, chloropenozide, chloropropylate, chlorphoxim, chlorpyrifos, chlorpyrifos methyl, chlorthiophos, clofentezine, CPCBS, CPMC, crotoxyphos, crufomate, cryolite, cufraneb, cyanofenphos, cyanophos, cyanthoate, cyfluthrin, cyhexatin, cypermethrin, cyphenothrin, cyromazine, DAEP, DDT, DDVP, deltamethrin, demeton, demeton-S-methyl, demeton-O-methyl, demeton-S, demeton-S-methyl sulfoxid, demephion-O, demephion-S, dialifor, diazinon, dicapthon, dichlofenthion, dicofol, dicrotophos, dieldrin, dienochlor, diflubenzuron, dihydrorotenone, dimefox, dimetan, dimethoate, dimethrin, dinex, dinitrophenol, dinobuton, dinocap, dioxabenzofos, dioxacarb, dioxathion, disparlure, disulfoton, DMCP, DNOC, d-trans allethrin, endosulfan, endothion, endrin, entice, EPBP, EPN, esfenvalerate, ethiofencarb, ethion, ethoate-methyl, ethoprop, etrimfos, fenamiphos, fenazaflor, fenbutatin-oxide, fenitrothion, fenoxycarb, fenpropathrin, fenson, fensulfothion, fenthion, fenvalerate, flubenzimine, flucythrinate, fluenethyl, flufenoxuron, fluvalinate, fonofos, formetanate hydrochloride, formothion, fosmethilan, fosthietan, furathiocarb, furethrin, grandlure, heptachlor, HETP, hexythiazox, hydramethylnon, hydroprene, IPSP, isazophos, isobenzan, isofenphos, isoprocarb, isoprothiolane, isothioate, isoxathion, jodfenphos, kinoprene, lead arsenate, leptophos, lethane, lindane, lythidathion, malathion, mazidox, mecarbam, mecarphon, menazon, mephosfolan, methamidophos, methidathion, methiocarb, methomyl, methoprene, methoxychlor, methoxyfenozide, methyl parathion, methyl phencapton, mevinphos, mexacarbate, MIPC, mirex, monocrotophos, MTMC, naled, nicotine, nonachlor, omethoate, ovex, oxamyl, oxydeprofs, oxydisulfoton, oxythioquinox, paraoxon, parathion, paris green, permethrin, perthane, phencapton, phenthoate, phorate, phosalone, phosfolan, phosmet, phosnichlor, phosphamidon, phoxim, pirimicarb, pirimiphos-ethyl, pirimiphos-methyl, plifenate, profenofos, promecarb, propargite, propetamphos, propoxur, prothidathion, prothiophos, prothoate, PTMD, pyridaben, pyridaphenthion, quinalphos, resmethrin, ronnell, rotenone, ryania, s-bioallethrin, salithion, schradan, sodium fluosilicate, sophamide, sulfotepp, sulprofos, tebufenozide, tefluthrin, temephos, TEPP, terbufos, tetrachlorvinphos, tetradifon, tetramethrin, tetrasul, thallium sulfate, thiocarboxime, thiocyclam hydrogenoxalate, thiometon, tolclofos-methyl, toxaphene, triazamate, triazophos, trichlorfon, trichloronate, triflumuron, trimethacarb, vamidothion, and xylylcarb;

b) 5–80% by weight of at least one water insoluble polymer prepared in emulsion selected from one or more homopolymers and copolymers independently comprising polymer units derived from: (1) one or more acrylic ester monomers; acrylamide or substituted acrylamides; styrene or substituted styrenes; butadiene; vinyl acetate or other vinyl esters; vinyl chloride, vinylidene chloride, N-vinyl pyrolidone or related vinyl monomers; acrylonitrile, and methacrylonitrile wherein the water insoluble polymer has a glass transition temperature between 0 and 60 degrees Celcius (° C.) and (2) ethylene and vinyl esters wherein the water insoluble polymer has a glass transition temperature between −20 and 40° C.; and c) 1–40% by weight of at least one water soluble polymer selected from non-ionic polymers comprising, polymers and copolymers comprising units derived from one or more of polyvinyl alcohol, partially hydrolyzed copolymers of vinyl esters, methyl methacrylate, and methacrylic acid wherein the non-ionic polymer has a molecular weight greater than 2,000 atomic mass units;

wherein the composition, when sprayed on a hydrophobic substrate, has improved resistance to wash-off by rain relative to the composition without the polymers.

* * * * *